United States Patent [19]

Oswald

[11] 4,390,729
[45] Jun. 28, 1983

[54] PROCESS FOR CARBONYLATION USING TETRAALKYL PHOSPHONIUM SUBSTITUTED PHOSPHINE AND AMINE TRANSITION METAL COMPLEXES AS CATALYST

[75] Inventor: Alexis A. Oswald, Mountainside, N.J.

[73] Assignee: Exxon Research and Engineering Co., Florham Park, N.J.

[21] Appl. No.: 204,245

[22] Filed: Nov. 3, 1980

Related U.S. Application Data

[62] Division of Ser. No. 114,627, Jan. 23, 1980, Pat. No. 4,302,401.

[51] Int. Cl.³ ............... C07C 45/50; C07F 15/00
[52] U.S. Cl. ................... 568/454; 568/453; 568/455; 568/882; 568/909; 260/429 R; 252/431 N; 252/431 P
[58] Field of Search ............ 568/453, 454 P, 455 N, 568/882, 909; 252/431 P, 431 N; 260/448 C

[56] References Cited

U.S. PATENT DOCUMENTS

| | | | |
|---|---|---|---|
| 3,709,979 | 1/1973 | Chu | 260/448 C |
| 3,929,849 | 12/1975 | Oswald | 260/448 C |
| 3,939,188 | 2/1976 | McVicker | 260/429 R |
| 3,974,227 | 8/1976 | Berthoux et al. | 568/455 |
| 4,013,700 | 3/1977 | Cawse | 252/431 P |
| 4,052,461 | 10/1977 | Tinker et al. | 568/455 N |
| 4,136,103 | 1/1979 | Oswald | 260/448 C |
| 4,179,403 | 12/1979 | Kim et al. | 568/455 |
| 4,201,714 | 5/1980 | Hughes | 260/429 R X |

FOREIGN PATENT DOCUMENTS 988943 4/1965 United Kingdom ............ 568/454

*Primary Examiner*—Helen M. S. Sneed
*Attorney, Agent, or Firm*—Robert J. North

[57] ABSTRACT

Complexes of the formula

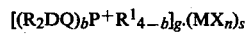

are disclosed in which R is selected from an alkyl group containing 1 to 30 carbon atoms and an aryl group containing from 6 to 10 carbon atoms; Q is a divalent organic radical selected from an alkylene group and an alkylene group the carbon chain of which is interrupted by an ether oxygen or phenylene group, wherein the alkylene group contains from 1 to 30 carbon atoms; $R^1$ represents an alkyl group containing from 1 to 30 carbon atoms, wherein said $R^1$ groups can be the same or different; D is a member selected from P and N; $Z^-$ is an anion; M is a Group VIII metal; X is an anion or organic ligand satisfying the coordination sites of the metal; b times g is 1 to 6; n is 2 to 6; and s is 1 to 3. Processes of using such complexes are also disclosed.

15 Claims, No Drawings

PROCESS FOR CARBONYLATION USING TETRAALKYL PHOSPHONIUM SUBSTITUTED PHOSPHINE AND AMINE TRANSITION METAL COMPLEXES AS CATALYST

This is a division of application Ser. No. 114,627, filed Jan. 23, 1980, now U.S. Pat. No. 4,302,401.

BACKGROUND OF THE INVENTION

The present invention relates to transition metal complexes and the use thereof as catalysts. More particularly, the present invention relates to transition metal catalysts containing phosphine or amine-type ligands and the use thereof in catalytic reactions, such as hydroformylation and combined hydroformylation/aldolization reactions.

Transition metal complexes of both triphenyl phosphine and trialkyl phosphines have been widely studied as catalysts for hydroformylation, hydrogenation, etc. For their application in reactions of carbon monoxide, particularly carbonylations, see the monograph of Juergen Falbe, "Carbon Monoxide in Organic Synthesis," Springer Verlag, New York, 1970. In the area of rhodium catalyzed hydroformylations of alpha-olefins, homogeneous catalyst systems and employing triaryl phosphine and other trivalent phosphorus compounds in complex with rhodium plus excess phosphine ligand were described by R. L. Pruett and J. A. Smith in U.S. Pat. No. 3,527,809.

Certain transition metal complexes containing phosphines covalently anchored to polymeric substrates have also been disclosed as heterogeneous catalysts. Such polymer anchored complexes were reviewed by C. C. Leznoff in Volume 3, pages 65 to 85 of the *Chemical Society Review* in 1974. The polymer anchored rhodium hydroformylation catalysts were also discussed in detail in the *Journal of Organometallic Chemistry*, Vol. 134, pages 85 to 94 in 1977 by W. H. Lang, A. T. Jurewicz, W. O. Haag, D. D. Whitehurst and L. L. Rollmann. Other complexes covalently anchored to inorganic solids such as silica were disclosed in a number of U.S. patents such as U.S. Pat. No. 3,726,809 by K. G. Allum, S. McKenzie and R. C. Pitkethly and U.S. Pat. No. 4,151,114 by A. A. Oswald and L. L. Murrell.

Still other patents have described bis-phosphine compounds as complexes for Rh. For example, Booth in U.S. Pat. Nos. 3,965,192 and 3,560,539 discloses ethylene bis-(diphenylphosphine) as a ligand for rhodium complexes.

In addition, layered tetraalkyl phosphonium clays were disclosed in my U.S. Pat. Nos. 3,929,849 and 4,053,493. In the second of these patents, diphenylphosphinodecyl is mentioned as a possible substituent for the phosphonium clays. However, there is no disclosure or suggestion in these patents of transition metal complexes of such phosphonium clay materials.

SUMMARY OF THE INVENTION

In accordance with the present invention, complexes of the formula

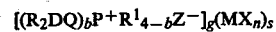

have now been discovered. Furthermore, it has been unexpectedly found that these complexes provide advantageous characteristics when used in connection with hydroformylation and combined hydroformylation/aldolization reactions. Specifically, the structure of the complexes have been found to provide control of their solubility, i.e., by the groups attached to the phosphonium group. For example, soluble quaternary phosphium complexes can be insolubilized via ion exchange of the counterion of the quaternary phosphonium cation with a suitable insoluble counterion species. These solubility properties, coupled with the catalytic properties of the complexes, allow advantageous application of the complexes in hydroformylation and other catalytic reactions. They are also useful for transition metal recovery for catalyst reprocessing. Accordingly, the present invention provides a process for recovering transition metals comprising reacting a transition metal compound with a member selected from a tetraalkyl phosphonium substituted tertiary phosphine and a tetraalkyl phosphonium substituted amine to form a complex and separating said complex from the reaction mixture. In such a recovery process, a preferable ligand member is a tetraalkyl phosphonium clay substituted tertiary phosphine or amine.

In the above formula R is independently selected from an alkyl group containing 1 to 30 carbon atoms and an aryl group containing from 6 to 10 carbon atoms; Q is a divalent organic radical selected from alkylene groups and an alkylene group the carbon chain of which is interrupted by ether oxygen or phenylene groups, wherein the alkylene group contains from 1 to 30 carbon atoms; $R^1$ represents an alkyl group containing from 1 to 30 carbon atoms, wherein said $R^1$ groups can be the same or different; $Z^-$ is an anion; M is a Group VIII metal; X is an anion or organic ligand satisfying the coordination sites of the metal; b times g is 1 to 6; n is 2 to 6; and s is 1 to 3.

In preferred embodiments of this invention, the complexes of the invention have the formulas

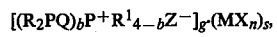

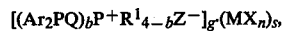

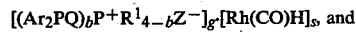

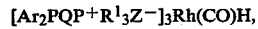

wherein Ar represents an aryl group containing from 6 to 10 carbon atoms, and R, Q, $R^1$, b, $Z^-$, g, M, n and s are as defined above. Particularly preferred complexes of the invention have the formula

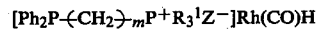

wherein Ph represents phenyl, m is an integer of from 1 to 30, and $R^1$ and $Z^-$ are as defined in above.

The properties which distinguish the present phosphine-phosphonium and amine-phosphonium transition metal complexes from the large variety of known transition metal catalysts are due to the presence of quaternary tetraalkyl phosphonium cations, preferably phosphonium cations covalently bound to the phosphorus of the phosphine ligand or to the nitrogen of the amine ligand via an alkylene bridge. This bonding is very stable and provides a permanent positive charge to the phosphine or amine ligand and its transition metal complex. The whole moiety is, of course, electrically neutralized by the corresponding mono- or poly-valent anion $Z^-$. This anion can be either a hydrated hydrophilic, primarily water soluble species, a lipophilic species soluble in a variety of organic solvents, a multivalent crosslinked organic anion, or an inorganic mineral anion. The type of anion in the present complexes can be readily interchanged via known methods of ion exchange and acid-base chemistry.

Taking advantage of ion exchange reactions, the present complexes can be readily solubilized or made insoluble. The phosphonium "handle" thus provides a unique, reversible means for making soluble, homogeneous or insoluble heterogeneous, transition metal catalysts, as desired, and for recovering such catalysts.

The R substituents on the phosphine or amine portion of the complexes of the present invention are selected to provide the desired catalyst activity and selectivity for the transition metal complex. For some transition metal complex catalysts, trialkyl phosphine ligands are preferred, i.e., both R groups are alkyl, preferably $C_1$ to $C_6$ alkyl. In other processes, varying degrees of aromatic character are desirable. In another preferred case both R groups are aryl, preferably those containing 6 to 10 carbon atoms in the basic aromatic structure, and more preferably phenyl. In the case of the amine phosphonium complexes of the invention, the R groups are preferably alkyl groups, and more preferably those containing from 1 to 6 carbon atoms.

The $R^1$ alkyl groups on the phosphonium portion of the complexes of the invention are selected to provide some of the desired solubility characteristics and ion pairing properties for the complexes of this invention. For increased solubility, lower alkyl and/or branched alkyl groups are desired. In general, lower alkyl groups provide a higher polar, i.e., hydrophilic character. An increasing carbon number of the alkyl groups reduces polarity and thus increases the lipophilic character of the complex. Branched, bulky alkyl groups lead to more ion separation, i.e., looser ion pairs.

The Q organic radical provides bridging of the phosphine or amine to the phosphonium phosphorus atoms. Therefore, the considerations in selecting Q are a sum of those for selecting R and $R^1$. To avoid opposing effects, the Q organic bridge is preferably long. A long, flexible alkylene bridge, such as a polymethylene chain, is also preferred for more effective catalysis.

The R, $R^1$ and Q groups can also be substituted with various substituent groups. As with the R, $R^1$ and Q groups themselves these substituents are selected with the above special considerations in mind. In general, these substituents on the R, $R^1$ and Q groups, and for that matter any substituent in the complexes of the invention, are those which are chemically unreactive with the reactants used in and the products of the desired catalyzed reaction, e.g. a hydroformylation or hydrogenation reaction. The same exemplary substituents can be used for any of the R, $R^1$ and/or Q groups. In general, the substituent organic groups have 1 to 30, preferably 1 to 12 carbon atoms. Other suitable substituents include hydrocarbyloxy such as alkoxy or phenoxy; acyl; acyloxy such as carbohydrocarbyloxy; unreactive halogen such as aromatic chlorine; aliphatic fluorine; and hydroxy groups.

The terminology "aryl group containing from 6 to 10 carbon atoms", as used in this specification and in the attached claims, is meant to include aromatic groups containing 6 to 10 carbon atoms in the basic aromatic structure which groups, however, can also be substituted with any chemically unreactive substituents as discussed above. The aromatic groups can also include heterocyclic aromatic groups such as pyrryl and furyl. Examples of the suitable aromatic groups are phenyl, fluorophenyl, difluorophenyl, chlorophenyl, tolyl, xylyl, benzoyloxyphenyl, carboethoxyphenyl, acetylphenyl, ethoxyphenyl, phenoxyphenyl, biphenyl, naphthyl, hydroxyphenyl, carboxyphenyl, trifluoromethylphenyl, tetrahydronaphthyl, methoxyethylphenyl, acetamidophenyl and dimethylcarbamylphenyl groups.

The terminology "alkyl groups containing from 1 to 30 carbon atoms", as used in this specification and in the attached claims to define and R and $R^1$ groups, is meant to include alkyl groups containing 1 to 30 carbon atoms in the basic alkyl structure which can be straight-chain, branched or cyclic and which can be substituted with any of the chemically unreactive substituents mentioned above. The alkyl groups are preferably primary or secondary alkyl groups and more preferably primary alkyl groups. In a preferred embodiment, the alkyl groups contain from 2 to 22 carbon atoms, and more preferably from 6 to 14 carbon atoms. Exemplary alkyl groups include methyl, ethyl, propyl, n-butyl, iso-butyl, t-butyl, n-hexyl, docosyl, triacontyl, fluoropropyl, perfluoroethyl, isopropyl, cyclopentyl, cyclohexyl, methoxyethoxyethyl, acetylethyl, tris-hydroxy substituted t-butyl triphenylmethyl, hydroxypropyl, and phenoxyethyl groups.

The phosphine phosphorus atom and amine nitrogen atoms are linked to the phosphonium phosphorus atom in the compounds of the present invention via a divalent organic radical Q selected from an alkylene group and an alkylene group the carbon chain of which is interrupted with an ether oxygen or phenylene group, wherein the alkylene group contains from 1 to 30 carbon atoms, preferably from 2 to 22 carbon atoms and more preferably from 2 to 4 carbon atoms. The terminology "alkylene group", as used in this specification and the attached claims, is meant to include an alkylene group containing 1 to 30 carbon atoms in the basic alkylene structure which may be substituted with any of the chemically unreactive substituents mentioned above. Q is preferably a polymethylene radical or a polymethylene radical. In another preferred embodiment, Q is a polymethylene radical the carbon chain of which is interrupted by an ether oxygen or a phenylene group. Exemplary Q groups include ethylene, butylene, docosamethylene, tricontamethylene, phenyl bis-(ethyl), ethylene bis-(oxyethyl), ethylene-bis oligo-(oxyethyl), oxy ethyl propyl, oxy ethyl perfluoroethyl, oxy ethyl hydroxypropyl.

$Z^-$ in the above formulas represents the counterion to the phosphonium cation in the complexes of the present invention. The counterion is preferably a noncoordinating anion. Examples of such suitable counterions are mono and polyvalent anions including halide, hydroxide, clay, aluminosilicate, sulfate, sulfonate, silicate, phosphate, phosphonate, phosphite, tetraphenyl boride, fluorophosphate, carboxylate such as acetate, phenoxide and alkoxide. When the valency of these anions is 1 to 4, the anion does not have a major effect on the solubility of the complex. However, polyanions having higher valency lead to insoluble complexes. Of course, in the case of polyvalent $Z^-$ anions, the number of phosphonium cations and phosphine complexes is correspondingly multiplied. Suitable examples of soluble anions include methanesulfonate, benzene sulfonate, ethanephosphonate, tolylphosphonate, hexafluorophosphate, acetate, benzoate, stearate, benzene disulfonate, and ethylene diamine tetraacetate.

A preferred $Z^-$ group comprises polyanions which can be derived from charged, crosslinked polymers, e.g., so-called ion exchange resins. These polyanionic $Z^-$ groups are either in the gel form or macroporous. Typical resins are copolymers of styrene and minor amounts of divinyl benzene with sulfonate or phosphonate groups attached to some of the benzene rings. Other strongly acidic resins are derived from perfluoroethylene with sulfonation. Weakly acidic resins having carboxylate groups are prepared, for example, via the copolymerization of methacrylic acid and divinyl benzene.

Another class of polyanions is inorganic in nature and is usually derived from minerals. In effect, most minerals are negatively charged. Certain aluminosilicates, particularly clays and zeolites, are preferred. These clays and zeolites, etc., can also be synthetic. A preferred type of clay has a layer structure. Such materials are discussed further below.

X in the above formulas represents an anion or organic ligand which satisfies the coordination sites of the metal M. Suitable X groups include $H^-$, alkyl$^-$, aryl$^-$, substituted aryl$^-$, $CF_3^-$, $C_2F_5^-$, $CN^-$, $N_3^-$, $COR^-$ (wherein R is alkyl or aryl), acetate, acetylacetonate, $SO_4^{2-}$, $PF_6^-$, $NO_2^-$, $NO_3^-$, $O_2^-$, $CH_3O^-$, $CH_2=CHCH_2^-$, CO, $C_6H_5CN$, $CH_3CN$, NO, $NH_3$, pyridine, $(C_4H_9)_3P$, $(C_2H_5)_3N$, chelating olefins, diolefins and triolefins, tetrahydrofuran, and triphenyl phosphine. Preferred organic ligands are those that are readily displaceable such as carbonyl, olefins, tetrahydrofuran and acetonitrile. The most preferred X ligands are CO and H.

The transition metal M can be any Group VIII metal. Suitable metals include Fe, Co, Ni, Pd, Pt, Rh, Ru, Ir and Os. Preferred Group VIII transition metals are Rh, Co, Ir and Ru, more preferably Rh and Co and most preferably Rh.

In the present complexes some of the organic ligands coordinatively bound to the transition metal are the tetraalkyl phosphonium substituted t-phosphines. Dependent on the types of these quaternary substituted phosphonium phosphines, different types of complexes are formed:

$[R_2PQP^+R_3^1Z^-]_g(MX_n)_s$; g=1-6

$[(R_2PQ_2)_2P^+R_2^1Z^-]_g(MX_n)_s$; 2g=1-6

$[(R_2PQ)_3P^+R^1Z^-]_g(MX_n)_s$; 3g=1-6

$[(R_2PQ)_4P^+Z^-]_g(MX_n)_s$; 4g=1-6

Among the tetraalkyl phosphonium phosphine transition metal complexes, preferably rhodium, of the invention, the preferred subgeneric classes are the following:

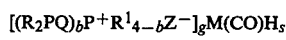
$[(R_2PQ)_bP^+R^1_{4-b}Z^-]_gM(CO)H_s$

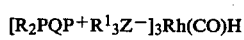
$[R_2PQP^+R^1_3Z^-]_3Rh(CO)H$

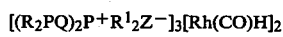
$[(R_2PQ)_2P^+R^1_2Z^-]_3[Rh(CO)H]_2$

$[(R_2PQ)_3P^+R^1Z^-]Rh(CO)H$ wherein R, $R^1$, Q, b, $Z^-$ and g are as defined above. In these complexes the preferred meaning of R is an aryl group containing 6 to 10 carbon atoms, especially phenyl; s is preferably 1 to 3; and g is 1 to 3. Every rhodium is preferably complexed with 2 or 3 phosphine phosphine atom, preferably with 3 phosphine moieties.

Some specifically preferred phosphine rhodium complexes possess phosphonium substituents bridged by a polymethylene group $[R_2P(CH_2)_mP^+R^1_{4-y}Z^-]_g[Rh(CO)H]_s$ wherein m is an integer of from 2 to 22, preferably from 3 to 22, more preferably from 6 to 14 and the meaning of the other symbols is as previously defined. Among preferred examples of such compositions are the following:

$[Ph_2PCH_2CH_2P^+(C_8H_{17})_2C_2H_5PhSO_3^-]_3Rh(CO)H$
$[Ph_2PCH_2CH_2CH_2P^+[CH_2CH(CH_3)_2]_3Ph_4B^-]_3Rh(CO)H$

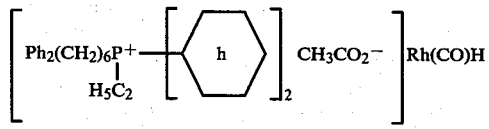

$(C_6H_{13})_2PCH_2CH_2CH_2P^+(C_6H_{13})_3PhCO_2^-$
$[(Ph_2CH_2CH_2CH_2)_2P^+(C_{12}H_{24})_2CH_3SO_3^-]_3Rh(CO)H$, and
$[(Ph_2CH_2CH_2CH_2)_3P^+C_2H_5PhSO_3^-]Rh(CO)H$ wherein Ph represents phenyl.

Examples of other preferred transition metal complexes are $[(C_2H_{17})_2P(CH_2)_2P^+(C_8H_{17})_2 PhSO_3^-]Co(CO)H$, $([Ph_2P(CH_2)_{14}P^+(C_4H_9)_2]Ph_4B^-)Ru(CO)H$, and $[(C_4H_9)PCH_2CH_2CH_2P^+(C_6H_{13})_3PF_6^-]_3Ir(CO)H$ again wherein Ph represents phenyl.

Although the above subgeneric formulas all contain phosphine ligand moieties, it should be understood that in these ligands N could be substituted for P. The preferred amine ligands have trialkyl amine moieties, i.e., in $R_2N$, R means $C_1$ to $C_{30}$ alkyl. Preferred generic formulas are the following:

$[R_2NQP^+R_3^1Z^-]_g(MX_n)_s$; g=1-6

$[(R_2NQ)_bP^+R_{4-b}Z^-]_gM(CO)H$; b times g is 1 to 6

A preferred class of complexes within the scope of the invention are those containing as the phosphonium counterion, a negatively charged, insoluble polymer, such as an ion exchange resin or an insoluble inorganic oxide such as an aluminosilicate, e.g., clay. A preferred class of such complexes is the rhodium complexes of clay of the formula $[R_2PQP^+R_3^1Clay^-]RhX_n$ wherein R, $R^1$, Q, X and n are as previously defined. In such formula, the clay to phosphine and clay to rhodium ratios depend on the ion exchange capacity of the clay to the reagents employed.

The Clay$^-$ groups of the present phosphonium compositions include modified clay groups which are best defined in terms of the layer type natural and synthetic metal and ammonium aluminosilicates from which they are derived. Natural clay starting materials can also be employed, including fine grained metal aluminosilicates which develop plasticity when mixed with limited amounts of water. For a more detailed definition and classification of clays, see the monograph entitled "Clay Mineralogy" by R. E. Grim, published by McGraw-Hill, Inc., New York, in 1968, particularly Chapters 1 to 3 on pages 1 to 50. Similar synthetic clay derivatives are also included. Preferred synthetic clay-like minerals are described in U.S. Pat. No. 3,671,190, the disclosure of which is incorporated herein by reference.

In general, sodium aluminosilicate clays are preferred for the derivation of the present phosphonium clays and complexes. The preferred clays have high cation exchange capacities and are crystalline. Among the preferred clays are those having crystalline layer type structures. For example, the three-layer type sodium montmorillonite clays can be advantageously used. Synthetic montmorillonites, e.g., laponites, are also suitable. Another useful clay is the chain structure type attapulgite. Two layer type clays such as kaolinites can be also used. Zeolites, i.e., metal or ammonium aluminosilicates having a tunnel-hole structure are not included in the term "clay" as it is used in the present invention.

Further examples of clays are halloysite, smectite, illite, vermiculite, chlorite, sepiolite, polygorskite, saponite, montronite, muscovite, beidellite, biotite, micas, talcum, batavite, allevardite, stevensite and amesite.

The processes for preparing the clay salts and the rhodium complexes thereof are disclosed in my U.S. Pat. No. 4,136,103, the disclosure of which is incorporated herein by reference.

The tetraalkyl phosphonium phosphine and amine ligands of the present complexes are preferably prepared from unsaturated tertiary phosphines, unsaturated phosphonium salts and bis- or poly-phosphines. In general, the synthesis and the physical properties of these intermediates is discussed in a series of monographs, entitled "Organo-phosphorus Compounds" by G. M. Kosolapoff and L. Maier, particularly in Volume 1, Chapter 1 by L. Maier, published by J. Wiley and Sons, Inc., New York, N.Y. in 1972. In the following, those synthetic methods are discussed which are particularly advantageous.

Preferred unsaturated t-phosphines are omega-alkenyl phosphines. They can be reacted with phosphines to provide the corresponding bis-phosphine adducts. For example, in a preferred case the following reaction takes place starting with a non-conjugated alpha, omega-diene $$CH_2=CH(CH_2)_{m-4}CH=CH_2 \xrightarrow{R_2PH} R_2P(CH_2)_{m-2}CH=CH_2$$

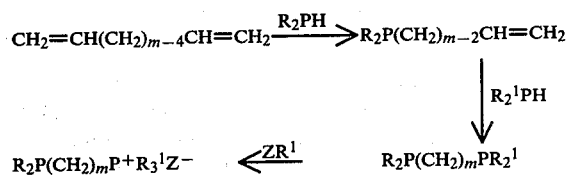

wherein the meaning of the previously used symbols is the same; however, the $ZR^1$ is an alkylating agent preferably alkyl halide or alkyl hydrocarbon sulfonate, such as ethyl methane sulfonate or propyl benzene sulfonate.

The addition reactions of the above scheme proceed via a free radical mechanism with chemical or radiation, preferably radiation initiation. It has been found that the selectivity of such reactions is improved by using an excess of phosphine reactant, preferably from 5 to 100% excess over the stoichiometric amount required of the phosphine.

As a chemical initiator, preferably a labile azo compound such as azo-bis-i-butyronitrile is used. The amount of the initiator varies depending on the chain length of the reaction from about 0.1 to 3%. The reaction temperature of chemically initiated additions depends at the temperature necessary for radical generation, which is usually in the 0° to 50° C. range.

For radiation initiation of the radical addition reaction, ultraviolet light or gamma-irradiation are particularly preferred. The radiation intensity and duration are again highly dependent on the chain length, i.e., G value. The preferred temperature for radiation initiation is between −90° and +90° C.

The alkylation of the bis-phosphine intermediates occurs selectively at the more aliphatic phosphine moiety. A selective quaternarization occurs in the manner indicated when R is aryl and $R^1$ is alkyl. However, both R and $R^1$ can be alkyl. For the quarternarization, equimolar alkylating reagents are preferred. The reaction occurs simply by heating the reaction mixture at the appropriate temperature. In the case of sulfonate ester alkylating agents the preferred temperature is between 20° and 80° C. A similar sequence of reactions can be carried out with alpha, omega-alkenyl ethers and divinyl benzene.

Another alternative displacement approach for the preparation of the unsaturated phosphines is via Grignard reactions of 1-alkenyl, preferably vinyl or allyl magnesium halides, with halophosphines, e.g.:

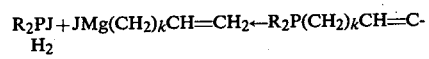

wherein J is Cl, Br or I; k is 0 to 28, preferably 0 or 1, and the other symbols are as previously defined.

Phosphinoalkyl halides can also be used to prepare the unsaturated phosphine intermediates via reactions with phosphides,

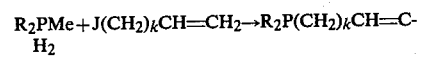

wherein Me is Li, K or Na and the other symbols are as previously defined.

Unsaturated amines are synthesized by similar displacement reactions plus by the reaction of free amine bases with alkylating agent such as alkyl halides.

Another preferred intermdiate is an unsaturated tetraalkyl phosphonium salt, which provides the desired phosphonium phosphine ligands via addition reactions, e.g.:

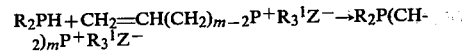

wherein the symbols have the meanings previously given. These additions are carried out via a free radical mechanism in a manner discussed previously for unsaturated phosphine additions.

Similar reactions can be used to prepare phosphonium substituted polyphosphines, e.g., according to the following general equation:

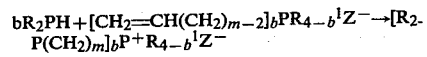

wherein the meaning of the symbols is the same as previously defined.

The counteranions of the phosphonium substituted t-phosphines prepared via the above methods generally have an ionic charge of from 1 to 4, preferably they are mono-charged. Also, some of the counterions such as the chlorides are undesirable for the catalytic complexes to be prepared. Consequently, these anions are often exchanged for more desirable anions either before or after the preparation of the transition metal complexes. The ion exchange preferably precedes complexation with the metal M. The anion to be introduced is preferably more lipophilic or insoluble in general. This method can be employed with transition metal preparations. A preferable method of ion exchange is to react a halide with a soluble metal salt of the parent acid of the desired anion, e.g.:

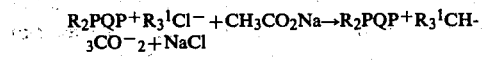

$R_2PQP^+R_3^1Cl^- + CH_3CO_2Na \rightarrow R_2PQP^+R_3^1CH_3CO^-_2 + NaCl$ wherein the symbols again have the meanings given above.

A similar ion exchange occurs with water dispersible sodium aluminosilicate clays, e.g.:

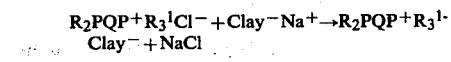

$R_2PQP^+R_3^1Cl^- + Clay^-Na^+ \rightarrow R_2PQP^+R_3^1\text{-}Clay^- + NaCl$

The resulting phosphonium clay derivative precipitates from water, but is dispersible in hydrocarbons. Such exchange reactions are disclosed in U.S. Pat. No. 4,136,103 by A. A. Oswald.

For the preparation of the transition metal complexes of the invention, standard methods or organometallic chemistry can be used, e.g., the methods discussed in a comprehensive text, "Advanced Inorganic Chemistry," by F. A. Cotton and G. Wilkinson (Interscience Publishers, New York, 1972) and exemplified in the series on "Inorganic Synthesis" particularly Volume XV, edited by G. W. Parshall and published by McGraw-Hill Book Co., New York, 1974.

A preferred method of synthesis of the complexes of the present invention is the reaction of transition metal carbonyl or diene complex or transition metal salts such as chloride salts, organic acid salts (e.g., acetates), and oxides, with the desired tetraalkylphosphonium substituted phosphine ligand. Particularly, for the preparation of hydroformylation catalysts CO and/or $H_2$ are used as additional reactants. These methods often include the displacement of a ligand of the intermediate, e.g., displacement of diolefin ligand from a complex by the phosphonium phosphine ligand of the present invention.

A specially preferred method reacts the corresponding transition metal, preferably rhodium, complex of a triaryl phosphine with the present phosphonium phosphine ligand. This ligand displacement method preferably uses the triphenyl phosphine complex of a transition metal carbonyl hydride as the reactant. Most preferably, tris-(triphenyl phosphine) rhodium carbonyl hydride and an excess of the present phosphonium phosphine or phosphonium amine ligand. Generally, the reaction is the following:

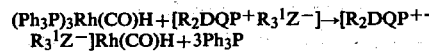

$(Ph_3P)_3Rh(CO)H + [R_2DQP^+R_3^1Z^-] \rightarrow [R_2DQP^+R_3^1Z^-]Rh(CO)H + 3Ph_3P$ This reaction can be readily carried out in solution at ambient temperatures. It can be followed by $^{31}P$ nuclear magnetic resonance spectroscopy. Nmr shows that the single phosphorus signal of the phosphine group in the complex of the present invention exhibits a change in the chemical shift value and becomes split into a doublet by the rhodium as a result of the ion exchange.

Ligand exchange methods can be used for the preparation of the present complexes in situ, e.g., under hydroformylation conditions. For this purpose, the various rhodium carbonyls, and appropriate organic salts of rhodium carbonyl are particularly preferred. For example, acetylacetonato (AcAc) dicarbonyl rhodium can be reacted with hydrogen and an excess amount of the phosphonium-phosphine or phosphonium-amine ligand:

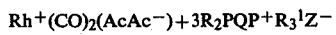

$Rh^+(CO)_2(AcAc^-) + 3R_2PQP^+R_3^1Z^-$

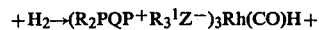

$+ H_2 \rightarrow (R_2PQP^+R_3^1Z^-)_3Rh(CO)H +$

$^3(CH_3CO)_2CH_2 + CO$

The complexes of the present invention have been found to be useful as catalysts in reactions where simple tertiary phosphines have previously been used, e.g., in hydrogenation, dimerization, polymerization and carbonylation reactions and combinations thereof. They are particularly useful in carbonylation reactions, especially hydroformylation reactions, which involve the reaction of unsaturated organic compounds with CO, or CO and hydrogen mixtures. Carbonylation reactions are generally reactions of unsaturated organic compounds with carbon monoxide plus preferably a third reactant. Carbonylations are described in detail in a monograph by Juergen Falbe, "Carbon Monoxide in Organic Synthesis," Springer, Verlag, New York, 1970. The main types of carbonylations catalyzed by the present complexes are the Roelen reaction (hydroformylation) of olefins with CO and $H_2$ and subsequent aldolization reactions; the Reppe reaction (metal carbonyl catalyzed carbonylation) mainly of olefins, acetylenes, alcohols and activated chlorides with CO alone or with CO plus either alcohol or amine or water; and ring closure reactions of functional unsaturated compounds such as unsaturated amides with CO. The unsaturated organic reactants are preferably olefinically unsaturated compounds, more preferably olefinic hydrocarbons.

A preferred carbonylation is an improved, selective hydroformylation comprising reacting an olefin with a mixture of carbon monoxide and hydrogen in the presence of a transition metal complex containing at least one tetraalkyl phosphonium-phosphine ligand to produce mainly an aldehyde, preferably via carbonylation at the less substituted vinylic carbon.

Organic non-hydrocarbon solvents, preferably of weak, nonsubstituted ligand character, are advantageously used as solvents for a hydroformylation process employing the tetraalkyl phosphonium phosphine transition metal complexes of the invention. Preferred solvents of ligand character are triaryl phosphines, such as triphenyl phosphine, triaryl stibines, and triaryl arsines. Other preferred organic solvents are ketones such as acetophenone and diphenyl ketone, polyethylene glycol, and organic silicone compounds such as diphenyl dipropyl silane. More preferred ligand solvents are triaryl phosphines.

In case of continuous hydroformylations of $C_2$ to $C_6$ olefins, particularly ethylene, wherein the volatile primary aldehyde reaction products are continuously removed, the nonvolatile secondary condensation products become the main solvents. The inert, nonvolatile oxygenated organic character, preferably of carboxylic ester and alcohol character, of these solvents make them particularly advantageous. They are further improved by the presence of a ligand type phosphine such as the phosphine-phosphonium ligand of the present invention.

The hydroformylation of olefins can also be performed in the present process in a manner coupling it with aldol condensation reaction by including an aldol condensation catalyst in the reaction mixture. For example, in the case of butene-1, the following conversions can be carried out in a combined process:

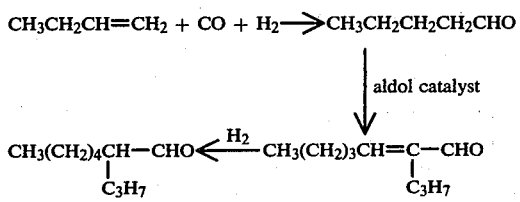

To realize such a conversion to an unsaturated or saturated aldol aldehyde, the present catalyst systems contain an aldol condensation catalyst such as KOH, NaOH or alkyl amines. Other known suitable aldolization catalysts are referred to in Volume 16, Chapter 1 of the monograph "Organic Reactions", edited by A. C. Cope et al., published by J. Wiley and Sons, Inc., New York, N.Y., 1968.

The carbonylation processes catalyzed by the complexes of the present invention can be carried out under the usual reaction conditions such as those described in the earlier referenced Falbe monograph. However, the reaction and particularly the hydroformylation of olefinic compounds, preferably olefins in the 2 to 40 carbon range, especially olefinic hydrocarbons such as mono-, di- and triolefins is advantageously carried out within a certain set of special conditions using tris-(diaryl phosphino tetraalkyl phosphonium) rhodium carbonyl hydride complexes of the invention as more fully explained below.

The olefinic reactants of the present hydroformylation can be terminally or internally unsaturated and or open chain or cyclic structure. The internal olefins must contain at least one, preferably two, hydrogens on the vinylic carbons. Terminal olefinic reactants, particularly alpha-olefins are preferred. Among the most preferred olefin reactants are $C_2$ to $C_6$ olefins, i.e., propylene, butene-1 and pentene-1, and ethylene.

Exemplary diolefin reactants are divinyl cyclohexane and 1,7-octadiene. Di- and polyolefin reactants are preferably nonconjugated in character.

Substituted olefinic reactants can also be used as long as the substituent does not interfere with the catalyst system and is stable under the reaction conditions. Exemplary substituted olefins are allyl alcohol, methyl oleate, 3-butenyl acetate, diallyl ether, allyl chlorobenzene.

The process of the invention, of course, employs a catalytic amount of the rhodium complex. The preferred concentration of the rhodium complex catalysts of the invention is in the range of $1 \times 10^{-6}$ to $1 \times 10^{-1}$ mole metal per olefin reactant. More preferred concentrations are in the range of $1 \times 10^{-5}$ to $1 \times 10^{-1}$ and the most preferred range is $1 \times 10^{-4}$ to $1 \times 10^{-2}$. Thus, the preferred rhodium concentration is normally in the range of from 10 to 1000 ppm. However, the preferred catalyst concentrations are directly affected by the concentration of free ligand present, especially the excess of the phosphine phosphonium ligand of the invention. The higher the ligand concentration, the higher the metal level required for a certain reaction rate.

In spite of the adverse effect on reaction rates, an excess of the ligand is employed in the hydroformylation processes of the invention mainly because higher free ligand concentration results in higher catalyst selectivity and stability. While I do not want to be bound by any theory, it is believed that the excess ligand affects the structure of the reactive catalyst species to provide these desired effects. In the case of alpha-olefins, the use of excess ligand results in a higher ratio of linear versus iso-isomers of the aldehyde products. For example, in the case of butene-1 hydroformylation, a higher ligand concentration provides a higher ratio of normal valeraldehyde to 1-methyl butyraldehyde

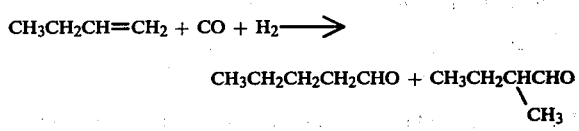

The preferred mole ratio of excess ligand to rhodium metal complex varies from 0.1 to 500. Mole ratios ranging from 5 to 300 are more preferred. In general, higher mole ratios are required more for maximum selectivity than for stabilization. Higher ratios are also employed when the desired operation is a continuous rather than a batchwise operation.

The selectivity of the present rhodium complex hydrogenation catalyst also depends on the molar ratio of the gaseous $H_2$ and CO reactants. This $H_2$/CO ratio should preferably be greater than 1, preferably in the range of 200 to 4.

The preferred process conditions of hydroformylations employing the catalyst of the present invention, especially the rhodium catalysts are unexpectedly mild. The preferred pressures are moderate; they are between 1 to 10,000 psi, preferably between about 1 and 1000 psi, and more preferably, between about 25 and 500 psi. The reaction temperatures are surprisingly low as far as hydroformylations are concerned. They are in the 80° to 200° C. range. Preferred temperatures are between 100° C. and 175° C. The broad operational temperature range is particularly unexpected. While high hydroformylation rates can be realized, for example at 100° C., hydroformylations can be also effected at 145° C. without a catastrophic loss of normal/iso selectivity or loss of catalyst activity through decomposition.

The present process can be carried out either in a homogenous liquid or with a heterogeneous solid plus liquid and/or gas. The catalysts can be employed as such or dissolved in a liquid or deposited on a solid such as clay silica, alumina or ion-exchange resin.

Particularly in the case of continuous process operation, the present carbonylations, especially the hydroformylation of terminal olefins, is advantageously carried out at a low olefin conversion, preferably at a 20 to 60% olefin conversion. In a preferred embodiment, low olefin conversion is coupled with a high ligand to rhodium ratio resulting in a particularly high ratio of linear to branched products, generally higher selectivity and improved catalyst stability, i.e., catalyst lift.

The following examples are intended to illustrate, but not limit, the present invention.

EXAMPLE 1

Addition of Diphenyl Phosphine to 1,13-Tetradecadiene

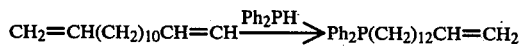

A magnetically stirred solution of an equimolar mixture of 93 grams (0.5 moles) of diphenyl phosphine and 97 g (0.5 moles) of 1,13-tetradecadiene in a closed cylindrical quartz tube was irradiated from about 3 cm distance with two 75 Watt Hanau tube immersion lamps with a wide spectrum of ultraviolet radiation, in a 15° C. water bath for 28 hours. A subsequent nmr analysis indicated a partial disappearance of the double bond due to the diphenyl phosphine addition. The resulting reaction mixture was fractionally distilled to recover the unreacted tetradecadiene and diphenyl phosphine and to obtain 70 g (35%) of 13-tetradecenyl diphenyl phosphine monoadduct as a clear colorless liquid distillate of bp. 185°–190° C. at 0.05 mm. The terminal olefinic unsaturation was clearly indicated by the nmr pattern of the vinylic portions of the distillate product. Anal. Calcd. for $C_{26}H_{37}P$; C, 82.06; H, 9.80; P, 8.14. Found: C, 82.02, H, 9.60; P, 8.32.

EXAMPLE 2

Addition of Di-i-Butyl Phosphine to 13-Tetradecenyl Diphenyl Phosphine $Ph_2P(CH_2)_{12}CH=CH_2 + [(CH_3)_2CHCH_2]_2PH \longrightarrow$ $Ph_2P(CH_2)_{14}P[CH_2CH(CH_3)_2]_2$ A mixture of 19.3 g (0.132 mole) di-i-butyl phosphine and 45.6 g (0.12 mole) 13-tetradecenyl diphosphine of Example 1 was reacted with u.v. irradiation as described in Example 1. After 48 hours irradiation at 15° C., there was about 40% reaction according to nmr analysis. Due to an increased viscosity and turbidity of the reaction mixture after a total of 14 hours irradiation at 15° C., the reaction temperature was raised to 63° C. at that point to obtain a clear homogeneous liquid. Irradiation was then continued at 63° C. for another 24 hours. At that point, the final olefinic reactant conversion was about 80%.

The reaction mixture was fractionally distilled in vacuo to obtain 40 g (63%) of 14-di-i-butylphosphinotetradecyl diphenyl phosphine as a clear yellow liquid, bp. 255°–260°/0.1 mm.

Anal. Calcd. for $C_{34}H_{56}P_2$; C, 77.52; H, 10.72; P, 11.76. Found: C, 77.79; H, 10.61; P, 10.94.

EXAMPLE 3

Selective Quaternarization of 14-Di-i-Butylphosphino-Tetradecyl Diphenyl Phosphine with Methyl n-Dodecylbenzene Sulfonate $Ph_2P(CH_2)_{14}+P[CH_2CH(CH_3)_2]_2 +$

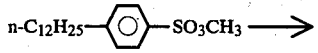

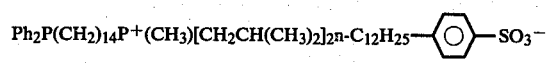

To 15.8 g (0.03 mole) of magnetically stirred 14-di-i-butylphosphino-tetradecyl diphenyl phosphine of Example 2, 10.2 g (0.03 mole) of methyl n-dodecylbenzene sulfonate ester was added to obtain a homogeneous liquid mixture. The preparation of the sulfonate reactant is disclosed in pending U.S. patent application Ser. No. 935,610 by A. A. Oswald and E. J. Mozeleski which was filed on Aug. 21, 1978. A slight (2° C.) rise of temperature on mixture indicated some reaction. To complete the desired quaternarization, the reaction mixture was heated to 80° C. and kept there for 2 hours. The resulting product was a highly viscous, colorless liquid at room temperature. Nmr analysis indicated that selective quaternarization occurred at the aliphatic phosphine group, i.e., 14-diphenylphosphino-tetradecyl di-i-butyl methyl phosphonium n-dodecylbenzene sulfonate was formed.

Anal. Calcd. for $C_{53}H_{88}O_3P_2S$: C, 73.40; H, 10.23; P, 7.14; S, 3.70. Found: 73.53, H, 10.19; P, 6.99; S, 3.58.

EXAMPLE 4

Addition of Diethyl Phosphine to 1,13-Tetradecadiene

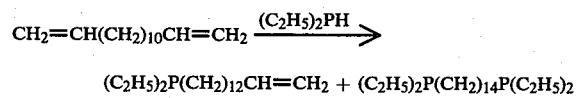

$(C_2H_5)_2P(CH_2)_{12}CH=CH_2 + (C_2H_5)_2P(CH_2)_{14}P(C_2H_5)_2$

An equimolar mixture of 27 g (0.3 mole) of diethyl phosphine and 60 g (0.3 m) of 1,13-tetradecadiene was reacted with u.v. initiation at 15° C. for 69 hours, in the manner described in Example 1. The resulting mixture was then fractionally distilled in vacuo. The monoadduct, 14-diethylphosphino-tetradecene was distilled between 126°–128° C. at 0.15 mm. The 36 g clear, colorless liquid obtained corresponds to about 41% of the calculated yield. The diadduct, bis-(1,14-diethylphosphino)-tetradecane was a higher boiling fraction between 177°–180° C. at 0.15 mm. It was also a clear colorless liquid. Its yield, 20 g, was about 35% of the theoretical. The assumed structures of both mono- and diadduct were supported by their respective nmr spectra.

Anal. Calcd. for the monoadduct, $C_{18}H_{37}P$: C, 76.00; H, 13.11; P, 10.89. Found: C, 76.07; H, 12.58; P, 10.78.—Calcd. for the diadduct, $C_{22}H_{48}P_2$: C, 70.54; H, 12.92; P, 16.54. Found: C, 71.55; H, 12.51; P, 15.12.

EXAMPLE 5

Addition of Diphenyl Phosphine to 14-Diethylphosphino Tetradecene-1

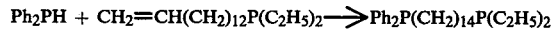

A mixture

Anal. Calcd. for $C_{30}H_{48}P_2$: C, 76.56; H, 10.19; P, 13.16. Found: C, 77.04, H, 10.07; and P, 13.37.

EXAMPLE 6

Quaternarization of 14-Diphenyl Phosphino-Tetradecyl Diethyl Phosphine with Ethyl Chloride $$Ph_2P(CH_2)_{14}P(C_2H_5)_2 + C_2H_5Cl \longrightarrow$$
$$[Ph_2P(CH_2)_{14}P^+(C_2H_5)_3]Cl^-$$

14.1 g (0.03 m) 14-Diphenyl phosphino tetradecyl diethyl phosphine from Example 5 was placed into a small pyrex tube equipped with a Teflon screw valve and a magnetic stirrer. The tube was then evacuated and exactly 2 g (0.03 m) ethyl chloride was condensed into it. The tube containing the mixture of the two reactants was then closed, heated with stirring to 150° C. and kept there for 24 hours. During the heating a lower quarternary bottom phase was formed and increased in volume until it became the only phase left. After the reaction, the viscous product was dissolved in a toluene-methanol mixture and transferred to a distilling flask. The solvents were then removed by heat 200° C. at 0.1 mm for 3 hours. The residual product obtained was a wax like colorless solid at room temperature. Nmr spectroscopy indicated that a selective quaternarization of the aliphatic phosphine moiety occured.

Anal. Calcd. for $C_{32}H_{53}P_2Cl$: C, 71.82; H, 9.98; P, 11.58; Cl, 6.62. Found: C, 71.29; H, 9.70; P, 11.39; and Cl, 6.59.

EXAMPLE 7

14-Diphenylphosphinotetradecyl Triethyl Phosphonium Montmorillonite and Its Complexing with 1,5-Cyclooctadiene Rhodium Chloride The starting clay was a refined sodium montmorillonite supplied by The Georgia Kaolin Co. of Elizabeth, N.J. It is available under the trade name Mineral Colloid BP (MCBP). This clay is prepared from a Penfield, Wyoming montmorillonite. The product has a water content of about 10%. Its composition corresponds to the following summary formula:

$(Si_{7.34}Al_{0.66}) \cdot Al_{3.18}Fe^{3+}{}_{0.37}Mg_{0.54}O_{20}(OH)_4Ca_{0.10}K_{0.04}Na_{0.68}$ This clay was indicated to have an ion exchange capacity of 90 me per 100 g. However, as indicated in my U.S. Pat. No. 4,136,103, it has been found that this clay has a minimum ion exchange capacity of 99 me per 100 g towards tetraalkyl phosphonium chlorides having at least one higher alkyl group. The present reactant was also employed at this level. The reaction temperature was 50° C. as usual. The details of the preparation were also the same as disclosed in Example 3 of my above referenced patent. The main steps of the procedure and the subsequent conversion to the rhodium complex derivative are given in the following, which corresponds to Example 18 of my U.S. Pat. No. 4,136,103.

To a stirred nitrogenated 0.85% suspension of 18.5 g dry (20.5 g wet) MCBP in 50% aqueous isopropanol, an 8.5% solution under nitrogen of 10 g (0.019 m) of 14-diphenylphosphinotetradecyl triethyl phosphonium chloride, also in 50% aqueous isopropanol was added during the course of a minute. Immediate reaction was indicated by a typical thickening of the mixture. After 30 minutes additional stirring, the product was filtered off with suction, washed and dried at 60° in the usual manner.

The above phosphinoalkyl phosphonium montmorillonite was ball-milled and screened using a 200 mesh screen. Of the screened phosphonium clay, 16.3 g was dispersed with stirring under nitrogen in a 0.25% benzene solution of 1.36 g (0.01 m) of 1,5-cyclooctadiene rhodium chloride dimer. A stable suspension resulted which was filtered with suction and washed three times with 50 ml nitrogenated benzene to provide the bright yellow solid clay complex product.

After drying overnight at room temperature at 0.1 mm. the product was analyzed for rhodium and phosphorus. The percentage values found were Rh, 1.94; P, 2.77. These values show that almost one atom rhodium was complexed per two phosphine moieties. The degree of rhodium removal from the benzene by complexation was about 60%.

EXAMPLE 8

Quarternarization of bis-1,14-Diethylphosphino-Tetradecane with Ethyl Benzene Sulfonate $$(C_2H_5)_2P(CH_2)_{14}P(C_2H_5)_2 + PhSO_3C_2H_5 \longrightarrow$$
$$(C_2H_5)_2P(CH_2)_{14}P^+(C_2H_5)_3 PhSO_3^-$$

The bis-phosphine compound of Example 7 is reacted with ethyl benzene sulfonate (in place of methyl n-dodecylbenzene sulfonate) in the manner described in Example 3 to produce the corresponding phosphonium substituted phosphine ligand.

EXAMPLE 9

Preparation of a Tris-(Phosphonium Substituted Alkyl Diphenyl Phosphine Substituted) Rhodium Carbonyl Hydride Complex Via Ligand Exchange

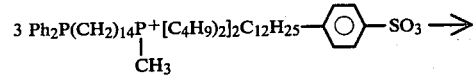

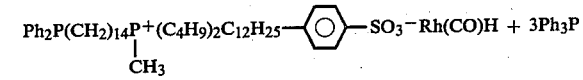

To a toluene solution of 14-diphenylphosphinotetradecyl-di-i-butyl methyl phosphonium 12-dodecylbenzene sulfonate, an equivalent amount of tris-(triphenyl phosphine) rhodium carbonyl hydride, was added to produce a 5% toluene solution for $^{31}P$ nmr studies. A similar solution of the phosphonium phosphine and a like solution of the complex were also separately studied. The results showed that the tris-(phosphonium phosphine) rhodium carbonyl hydride of the invention was formed via ligand displacement and that the new complex has a phosphine to rhodium coordination.

EXAMPLE 10

Addition of i-Butyl Phosphine To Allyl Dimethyl Amine (CH$_3$)$_2$CHCH$_2$PH$_2$ + 2 CH$_2$=CHCH$_2$N(CH$_3$)$_2$ ⟶

(CH$_3$)$_2$CHCH$_2$P[CH$_2$CH$_2$CH$_2$N(CH$_3$)$_2$]$_2$

A mixture of 37.4 g (0.44 mole) of allyl dimethyl amine and 18 g (0.2 mole) of i-butyl phosphine was reacted with u.v. initiation at 15° C. for 24 hours in the manner described in Example 1. Then it was fractionally distilled in vacuo to obtain 45 g (86.5%) of the adduct, i-butyl bis-(2-dimethylaminopropyl) phosphine, as a colorless liquid between 82°–83° C. at 0.1 mm.

Anal. Calcd. for C$_{14}$H$_{33}$PN$_2$: C, 64.58; H, 12.77; P, 11.89; N, 10.76. Found: C, 66.17; H, 11.98; P, 10.31; N, 10.84.

EXAMPLE 11

Selective Quaternarization of i-Butyl Bis-(Dimethylaminopropyl Phosphine) with n-Dodecyl Chloride (CH$_3$)$_2$CHCH$_2$P[CH$_2$CH$_2$CH$_2$N(CH$_3$)$_2$]$_2$ + CH$_3$(CH$_2$)$_{11}$Cl ⟶

$$\begin{array}{c}(CH_3)_2CHCH_2\\ \diagdown\\ \phantom{xx}P^+[CH_2CH_2CH_2N(CH_3)_2]_2Cl^-\\ \diagup\\ CH_3(CH_2)_{11}\end{array}$$

A magnetically stirred mixture of 15.6 g (0.06 mole) of i-butyl bis-(dimethylaminopropyl) phosphine of Example 10 and 12.3 g (0.06 mole) of n-dodecyl chloride was heated under nitrogen to 130° C. and then kept there for 24 hours. The nmr spectrum of a sample of the heated mixture showed a substantial selective quaternarization of the t-phosphine moiety. Accordingly, the crude mixture was heated at 150° C. at 0.2 mm. to distill off the volatile unreacted compounds and to obtain the residual product, i.e. bis-(3-dimethylaminopropyl) dodecyl i-butyl phosphonium chloride. The product weighed 23 g, 82% of the calculated yield, and hardened to a wax like solid at room temperature. Nmr indicated that quaternarization occurred at the phosphine group.

EXAMPLE 12

Preparation of Bis-(3-Dimethylaminopropyl) Dodecyl i-Butyl Phosphonium Montmorillonite Via Ion Exchange i-C$_4$H$_9$P$^+$(C$_{12}$H$_{25}$)[CH$_2$CH$_2$CH$_2$N(CH$_3$)$_2$]$_2$Cl$^-$ + Clay$^-$Na$^+$ ⟶ i-C$_4$H$_9$P$^+$(C$_{12}$H$_{25}$)[CH$_2$CH$_2$CH$_2$N(CH$_3$)$_2$]$_2$Clay$^-$ + NaCl Bis-(3-dimethylaminopropyl) dodecyl primary isobutyl phosphonium chloride (10.5 g, 0.0225 mole of Example 11) was reacted with 25 g (0.0225 mole equivalent) MCBP in the manner described in Example 7 to yield 30 g of the corresponding phosphonium montmorillonite.

Anal. Calcd.: C, 22.04; H, 4.13; P, 2.19; N, 1.98. Found: C, 22.07; H, 4.53; P, 1.82; N, 1.69.

The above amine substituted tetraalkyl phosphonium montmorillonite can be complexed with Co and Rh via known methods. The complexes are useful hydroformylation catalysts.

EXAMPLE 13

Addition of i-Butyl Phosphine To Allyl Diethyl Amine (CH$_3$)$_2$CHCH$_2$PH$_2$ + 2CH$_2$=CHCH$_2$N(C$_2$H$_5$)$_2$ ⟶

(CH$_3$)$_2$CHCH$_2$P[CH$_2$CH$_2$CH$_2$N(C$_2$H$_5$)$_2$]$_2$

A mixture of 56.7 g (0.5 mole) of allyl diethyl amine and 25.1 g (0.275 mole) of i-butyl phosphine was reacted and distilled as in Example 10. The adduct, i-butyl, bis-(3-diethylaminopropyl) phosphine, boiled 107°–108° C. at 0.05 mm. It was obtained in 86% yield (68 g) as a colorless liquid.

Anal. Calcd. for C$_{18}$H$_{41}$PN$_2$: C, 68.31; H, 13.06; P, 9.78; N, 8.85. Found: C, 69.41; H, 12.57; P, 10.15; N, 9.00.

The phosphine group of this product can be selectively quaternarized by sulfonate esters, e.g. ethyl toluene sulfonate, to provide the corresponding bis-(3-diethylaminopropyl) phosphonium sulfonate salts. The amine ligand groups of these salts can be complexed with cobalt and rhodium via known methods. The products are hydroformylation and hydrogenation catalysts in standard hydroformylation tests.

GENERAL METHOD OF HYDROFORMYLATION

The hydroformylation of butene-1 to provide linear pentanal and branched 2-methyl butanal products was selected for comparative studies of the catalytic properties of certain phosphonium substituted t-phosphine complexes of the invention. The complexes studied were either isolated before use or generated in situ from the known tris-(triphenyl phosphine) rhodium carbonyl hydride by the addition of the appropriate ligand material of the present invention in varying amounts. Tris-(triphenyl phosphine) rhodium carbonyl hydride in the presence of varying excess of triphenyl phosphine was used as a known catalyst standard for comparison.

The experiments were carried out in a 300 ml stainless steel (S) autoclave. The autoclave was equipped with a highly effective, impeller type stirrer, operating at 750 rpm during the experimental runs.

The standard hydroformylation procedure was the following: the appropriate amounts of complex being tested were dissolved in 100 g of the proper mixture of a free phosphine ligand and 2-propyl heptyl n-valerate solvent. Most often the amount of complex employed provided 100 ppm rhodium concentration. This meant 100 mg per kg, about 1 mmole per kg rhodium would be present in 1 kg starting mixture. The excess phosphine ligand added to the solvent was calculated to provide a free ligand to rhodium ratio (L/Rh) in the 5 to 140 range.

The 100 g rhodium complex-ligand solution was placed into the autoclave which was then deaerated by repeated pressurization with nitrogen. The solution under atmospheric nitrogen pressure was then sealed and heated to the reaction temperature.

When the solution reached the reaction temperature, 200 g liquid butene was pressured into the autoclave with a 1 to 4 carbon monxide-hydrogen mixture. The butene was followed by the CO/H$_2$ mixture until a pressure of 350 psig was reached. At that point, the supply of 1:4 CO/H₂ was shut off and the autoclave was connected to a cylinder of about 1 liter volume containing a 1:1 CO/H₂ mixture at 1000 psig. The connection was made through a pressure regulating valve set to provide the 1:1 CO/H₂ gas to the autoclave to maintain a 350 psig pressure during the reaction.

The progress of the hydroformylation was followed on the basis of the amount of 1:1 CO/H₂ consumed. The latter was calculated on the basis of the pressure drop in the 1 liter CO/H₂ cylinder. Reactant conversion calculated on the basis of CO consumption was plotted against the reaction time to determine the reaction rate. The reaction rate was expressed as the fraction of the theoretical CO/H₂ requirement consumed per minute (k min$^{-1}$). The reaction was discontinued when the reaction rate drastically dropped. Depending on the side reaction, such a butene-1 hydrogenation and butene-1 to butene-2 isomerization, the stability of the catalyst complex in the mixture, such a rate drop occurred generally between 80–90% conversion. Accordingly, the reactions were usually discontinued in that conversion range.

When the reaction was to be discontinued, the CO/H₂ feed valve was shut and the autoclave was immediately cooled with cool water. In case of low conversions, ice bath was used. When cooling was complete, the synthesis gas was released slowly. The residual liquid was visually observed for catalyst decomposition. A dark orange to brown color of the originally yellow mixture indicated increasing degrees of catalyst decomposition. Severe catalyst decomposition usually resulted in the precipitation of dark solids.

Analysis of the residual liquid mixture were carried out using gas chromatography. The liquids were analyzed in a gc instrument using flame ionization detector. By this instrument, the C₄ hydrocarbons were detected and measured as a single peak. The two isomeric C₅ aldehydes were completely separated. The ester solvent and the ligands were also clearly detected. Due to the lower response of this detector to the aldehydes, the intensity of the hydrocarbon peaks was multiplied usually by 0.7 to obtain the necessary concentration correction. The individual, gaseous C₄ hydrocarbons were separated from the liquids and then the individual components of the gas were chromatographed and detected by a thermal conductivity detector.

By this procedure the following hydroformylations were performed:

EXAMPLE 14

Hydroformylation with tris-(14-Diphenylphosphino-Tetradecyl Di-i-Butyl Methyl Phosphonium n-Dodecylbenzene Sulfonate) Ligand Rhodium Carbonyl Hydride Complex

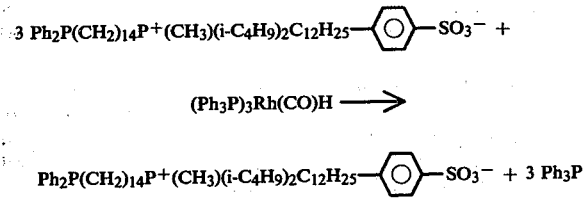

Tris-(triphenyl phosphine) rhodium carbonyl hydride, 0.1 g (0.1 mmole), was mixed with 80 g of a mixture of 4 g (14 mmole) of 14-diphenylphosphinotetradecyl-di-i-butyl methyl phosphonium n-dodecyl benzene sulfonate of Example 3 and 76 g 2-propylheptyl valerate to provide a catalyst system via the above ligand exchange. This system contains a 105 ppm rhodium concentration and a 108 fold ligand excess.

Butene hydroformylations were then carried out at 100° C. in the above-described manner. The results indicated the complexing of the phosphonium phosphine with resulting formation a novel catalyst complex. The rate value, k min$^{-1}$, was 0.009. At a 60 percent CO conversion level, the n/i ratio of the product was 4.4.

EXAMPLE 15

Hydroformylation with the Rhodium Carbonyl Hydride Complex 14-Diphenylphosphinotetradecyl Triethyl Phosphonium Montmorillonite Clay The rhodium chloride complex of 14, diphenylphosphinotetradecyl triethyl phosphonium montmorillonite clay, described in Example 7 was used as a catalyst precursor under hydroformylation conditions by reacting it with CO and H₂ to generate the corresponding rhodium carbonyl hydride catalyst:

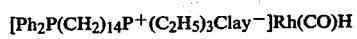

[Ph₂P(CH₂)₁₄P⁺(C₂H₅)₃Clay⁻]Rh(CO)H

A suspension of 5 g of the catalyst precursor in 75 ml of toluene was prepared. The carbonyl hydride catalyst was generated under standard hydroformylation conditions at 120° C. Under the same conditions, slow selective 1-butene hydroformylation to the corresponding aldehydes and a more rapid isomerization to 2-butenes occurred. The n/i ratio of aldehydes was about 0.7. The aldehyde selectivity was 13%, while the 2-butenes selectivity was 85%. On the basis of H₂/CO consumption, the hydroformylation rate, k min$^{-1}$, was 0.001.

EXAMPLE 16

Hydroformylation with the Rhodium Carbonyl Hydride Complex of 14-Diphenylphosphinotetradecyl Triethyl Phosphonium Montmorillonite Clay In the Presence Of Added Excess t-Phosphine The catalyst system of the previous example was tested under the same conditions in the presence of 3.3 g of n-butyl diphenyl phosphine. This phosphine represents an about 14 fold molar excess over the rhodium.

The standard hydroformylation test showed that the reaction rate remained about the same, but the selectivities changed drastically. The selectivity to aldehydes was 96%. The selectivity to 2-butenes was only 1.3%. The n/i ratio of aldehydes was 4.3.

It will be understood that the embodiments described above are merely exemplary and that persons skilled in the art may make many variations and modifications without departing from the spirit and scope of the invention. All such modifications and variations are intended to be included within the scope of the invention as defined by the appended claims.

I claim:

1. A process for carbonylation comprising reacting an organic compound capable of being carbonylated with CO in the presence of a catalyst complex of the formula:

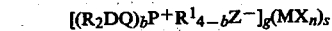

[(R₂DQ)ₑP⁺R¹₄₋ₑZ⁻]ₐ(MXₙ)ₛ wherein each R is independently selected from an alkyl group containing from 1 to 30 carbon atoms and an aryl group containing from 6 to 10 carbon atoms; D represents a member selected from P and N atoms; Q is a divalent organic radical selected from an alkylene radical and an alkylene radical the carbon chain of which is interrupted with ether oxygen or phenylene group, wherein said alkylene radical contains from 1 to 30 carbon atoms; $R^1$ represents an alkyl group containing from 1 to 30 carbon atoms, wherein said R1 groups can be the same or different; b is an integer of from 1 to 4; $Z^-$ is an anion; M represents a Group VIII metal atom; X is an anion or organic ligand satisfying the coordination sites of the metal M; b times g is 1 to 6; n is 2 to 6; and s is 1 to 3.

2. The process of claim 1 being a hydroformylation process comprising reacting an olefinically unsaturated organic compound with carbon monoxide, hydrogen and in the presence of a catalyst complex as defined in claim 1.

3. A process according to claim 2, wherein said transition metal complex is of the formula $$[(R_2PQ)_bP^+R_{4-b}{}^1 \cdot Z^-]_g[M(CO)H]_s$$

wherein each R is independently selected from an alkyl group containing from 1 to 30 carbon atoms and an aryl group containing from 6 to 10 carbon atoms; Q is a divalent organic radical selected from an alkylene radical and an alkylene radical the carbon chain of which is interrupted with ether oxygen or phenylene groups, wherein said alkylene radical contains from 1 to 30 carbon atoms; b is an integer of from 1 to 4; $R^1$ represents an alkyl group containing from 1 to 30 carbon atoms, wherein said $R^1$ groups can be the same or different; $Z^-$ is an anion; g times b is 1 to 6; M represents a Group VIII metal atom; and s is 1 to 3.

4. A process according to claim 2, wherein said transition metal complex is of the formula $$[Ph_2P(CH_2)_mP^+R_3{}^1Z^-]_3Rh(CO)H$$

wherein Ph represents phenyl, m is an integer of 1 to 30, $R^1$ represents an alkyl group containing from 1 to 30 carbon atoms, wherein the $R^1$ groups are the same or different, and $Z^-$ is an anion.

5. A process according to claim 4, wherein said complex is of the formula

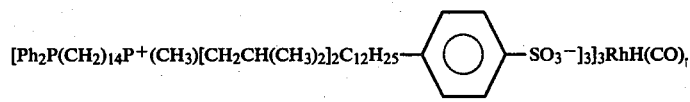

6. A process according to claim 3, wherein said transition metal complex is of the formula $$[Ph_2P(CH_2)_{14}P^+(C_2H_5)_3Clay^-]_3Rh(CO)H$$

7. The process of claim 1 wherein D in the formula is phosphorus.

8. The process of claim 1 wherein M in the formula is Co or Rh.

9. The process of claim 1 wherein Z in the formula is an aluminosilicate anion.

10. The process of claim 1 wherein $(MX_n)_s$ of the formula is $[M(CO)H]_s$.

11. The process of claim 2 wherein D in the formula is phosphorus and $Z^-$ is an inorganic polyanion.

12. The process of claim 2 wherein D in the formula is phosphorus and $Z^-$ is a noncoordinating anion with a valency of 1 to 4.

13. The process of claim 2 wherein $Z^-$ in the formula is a sulfonate anion.

14. The process of claim 2 wherein D in the formula is phosphorus and $Z^-$ is a noncoordinating anion.

15. The process of claim 2 wherein said catalyst complex is of the formula:

$$(R_2PQP^+R^1{}_3Z^-)_3Rh(CO)H$$

wherein R, Q, $R^1$ and $Z^-$ are previously defined.

* * * * *